United States Patent [19]

Gibson

[11] Patent Number: 4,942,228
[45] Date of Patent: Jul. 17, 1990

[54] PRODUCTION OF POLYOL POLYESTERS HAVING REDUCED COLOR CONTENT

[75] Inventor: Michael S. Gibson, Milford, Ohio

[73] Assignee: The Procter & Gamble Company, Cincinnati, Ohio

[21] Appl. No.: 860,285

[22] Filed: May 6, 1986

[51] Int. Cl.$^5$ .................. C07H 1/00; C07H 13/06; C07C 67/03; C07C 67/60

[52] U.S. Cl. .................... 536/119; 260/405.6; 260/410.6; 560/234; 560/248; 536/63

[58] Field of Search ............... 560/234, 248, 263; 260/410.6, 405.6; 536/119; 519/63

[56] References Cited

U.S. PATENT DOCUMENTS 3,600,186  8/1971  Mattson et al. .................. 99/1
3,984,444  10/1976  Ritz et al. ...................... 260/405.6
4,517,360  5/1985  Volpenhein ...................... 536/119
4,552,702  11/1985  Schmid et al. ................... 260/428

OTHER PUBLICATIONS

Fette-Seifen-Anstr., 1961, vol. 63, No. 5, pp. 413-420, Baltes et al.; Chem. Abstract 55:18139i also attached.
JAOCS, vol. 62, Feb. 1985, No. 2, pp. 331-335, Ogoshi et al.

Primary Examiner—Vivian Garner
Attorney, Agent, or Firm—Robert B. Aylor; Richard C. Witte

[57] ABSTRACT

Polyol polyesters having reduced color content are prepared by base-catalyzed transesterification of pretreated lower (i.e., $C_1$–$C_3$) alkyl fatty esters with polyols. the pretreatment comprises the steps of contacting the alkyl fatty esters (in a liquid state) with an alkoxide base, separating undissolved solids from the esters, and then distilling the esters.

11 Claims, No Drawings

PRODUCTION OF POLYOL POLYESTERS HAVING REDUCED COLOR CONTENT

TECHNICAL FIELD

This invention relates to the production of polyol fatty polyesters having reduced content of color bodies.

BACKGROUND OF THE INVENTION

The food and pharmaceutical industries have developed an interest in higher polyol polyesters of fatty acids for use as low calorie fats in food products and as pharmaceutical agents, e.g., for the lowering of blood cholesterol levels. U.S. Pat. No. 3,600,186, Mattson and Volpenhein, issued Aug. 17, 1971, describes low calorie food compositions formed by replacing at least a portion of the fat content of food products with higher polyol fatty acid polyesters. U.S. Pat. No. 3,954,976, Mattson and Volpenhein, issued May 4, 1976, describes pharmaceutical compositions for inhibiting the absorption of cholesterol comprising effective unit dosage amounts of higher polyol fatty acid polyesters, as well as the method for treating hypercholesterolemia using these polyesters. Additional pharmaceutical uses are described in U.S. Pat. No. 4,241,054, Volpenhein and Jandacek, issued Dec. 23, 1980 (removal of halogenated toxins from the body), and U.S. Pat. No. 4,264,583, Jandacek, Apr. 28, 1981 (treatment of gallstones).

The polyol polyesters are also useful as emulsifiers.

Typical syntheses of polyol polyesters involve reaction of lower monohydric alcohol esters (e.g. methyl esters) of fatty acids with the polyol. See for example U.S. Pat. Nos. 3,963,699 Rizzi et al., issued June 15, 1976; 4,518,722, Volpenhein, issued May 21, 1985 and 4,517,360, Volpenhein, issued May 14, 1985, all incorporated by reference herein.

The fatty lower alkyl esters used in the preparation of the polyol polyesters are typically derived from natural fats and oils such as soya oil, cottonseed oil, sunflower oil, etc. Such esters contain substantial quantities of conjugated and conjugatable cis and trans unsaturated fatty acid chains. When such fatty esters have been subjected to atmospheric oxidation (as indicated by measurement of their peroxide value), they have an even higher propensity to conjugate. When these esters are reacted with polyols in the presence of a basic catalyst (e.g., potassium carbonate) to produce the corresponding polyol polyesters, the resulting product is usually found to have a brownish-yellow color. Such color is undesirable, especially for situations where the polyol polyesters is to be used in foods or other consumer products.

An object of the present invention is to provide lower alkyl esters of fatty acids which, when converted to polyol polyesters by base-catalyzed transesterification with polyols, produce polyol polyesters having low color content.

Another objective of the present invention is to provide fatty polyol polyesters having reduced color content.

Another objective is to provide a process for preparing fatty polyol polyesters having reduced color content.

BACKGROUND ART

U.S. Pat. No. 3,984,444, Ritz et al., issued Oct. 5, 1976, discloses treatment of methyl esters of soya fatty acids with potassium methylate to isomerize nonconjugated double bonds in the polyunsaturated fatty chains to a conjugated form.

U.S. Pat. No. 4,552,702, Schmidt et al., issued Nov. 12, 1985, discloses treatment of lower alkyl esters of fatty acids with esterification catalysts (including inter alia, alkali metal alkoxides) at temperatures above 150° C. and separating the treated esters. The treatment is said to render the esters more suitable for further processing, e.g., sulfonation.

U.S. Pat. Nos. 3,963,699 and 4,517,360, cited supra, disclose the base-catalyzed reaction of polyols with methyl esters of fatty acids to produce polyol polyesters.

SUMMARY OF THE INVENTION

In preparing fatty polyol polyesters by reacting polyols with lower alkyl esters of fatty acids in which at least some of the fatty acid chains contain conjugated or conjugatable sites of unsaturation, the lower alkyl esters are pretreated (prior to reaction with the polyol) by a process comprising the steps of contact with an alkoxide base at from about 60° C. to about 140° C. for from about 10 minutes to about 120 minutes, followed by removal of undissolved solids and distillation. These pretreated lower alkyl fatty esters, when reacted with polyols to form polyol polyesters, provide a fatty polyol polyester reaction product having minimal color.

DETAILED DESCRIPTION OF THE INVENTION

One aspect of the present invention comprises a process for treatment of lower (i.e., $C_1$–$C_3$) alkyl esters of $C_6$–$C_{22}$ fatty acids wherein at least 0.1% of the fatty acid moieties contain conjugated or conjugatable sites of unsaturation. The process comprises the steps of:

(A) contacting said lower alkyl esters of fatty acids in a liquid state with an alkoxide base at a temperature of from about 60° C. to about 140° C. for from about 10 minutes to abut 120 minutes;

(B) separating undissolved solids from the liquid esters of Step A; and (C) distilling the liquid esters from Step B and collecting the distilled esters.

Another aspect of the invention is the preparation of polyol polyesters by reacting a polyol with the lower alkyl fatty esters which have been treated according to the above-described treatment process, in the presence of a basic catalyst, with concurrent removal from the reaction mix of the lower (i.e., $C_1$–$C_3$) alcohol which is formed during the reaction. This results in the production of polyol polyesters having color content which is substantially less than that of polyol polyesters which are prepared from lower alkyl fatty esters which have not been given the above-described treatment.

The preparation of the polyol polyesters from the treated lower alkyl fatty esters is accomplished by the known procedure of reacting the lower alkyl fatty esters with polyol in the presence of a basic catalyst such as alkali metal alkoxides, hydroxides, hydrides and carbonates. See, for example, U.S. Pat. Nos. 3,963,699, Rizzi et al., issued June 15, 1976; 2,893,990, Haas et al., issued July 7, 1959; 4,518,722, Volpenhein, issued May 21, 1985; and 4,517,360, Volpenhein, issued May 14, 1985; all incorporated by reference herein.

As used herein, the term "polyol" is intended to include any aliphatic or aromatic hydroxy compound containing at least two free hydroxyl groups. The selection of a suitable polyol is simply a matter of choice. For example, suitable polyols may be selected from the following classes: saturated and unsaturated straight and branched chain linear aliphatics; saturated and unsaturated cyclic aliphatics, including heterocyclic aliphatics; or mononuclear or polynuclear aromatics, including heterocyclic aromatics. Carbohydrates (e.g., monosaccharides) and nontoxic glycols are preferred polyols. Monosaccharides suitable for use herein include, for example, glucose, mannose, galactose, arabinose, xylose, ribose, apiose, rhamnose, psicose, fructose, sorbose, tagitose, ribulose, xylulose and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also included as preferred materials for use herein. The sugar alcohols most widely distributed in nature and preferred for use herein are sorbitol, mannitol and galactitol.

Particularly preferred classes of materials suitable for use herein include the monosaccharides, the disaccharides and sugar alcohols. Preferred carbohydrates and sugar alcohols include xylitol, sorbitol and sucrose.

As used herein, the term "lower alkyl fatty esters" refers to the $C_1$-$C_3$ alkyl esters of fatty acids containing from 6 to 22 carbon atoms in the fatty acid chain.

The lower alkyl fatty esters herein are derived from natural fats and oils in which the fatty acid moieties comprise those having chain lengths of 6 to 22 carbon atoms and wherein some of said fatty acid moieties have multiple sites of unsaturation which are either conjugated or conjugatable. The fatty acids from these oils are mixtures of saturated and unsaturated acids of various chain lengths. For example, methyl esters made from soybean oil will contain, inter alia, methyl palmitate, methyl stearate, methyl oleate, methyl linoleate and methyl linolenate. The lower alkyl fatty esters are typically prepared by alcoholysis of fats and oils or by hydrolysis of fats and oils followed by reaction of a lower alcohol with the free fatty acids produced by the hydrolysis. Examples of fats and oils from which the fatty acids are derived are lard, soybean oil, sunflower oil, safflower oil and corn oil. Specific fatty acids from fats and oils which contain multiple sites of unsaturation which are conjugated or conjugatable include linoleic, linolenic, eleostearic, arachidonic and parinaric acids. Typically the oils will be partially hydrogenated prior to their conversion to lower alkyl fatty esters.

While the present invention is not to be limited to any theory, it is believed that the conjugated and conjugatable sites of unsaturation are responsible for production of color bodies when the alkyl fatty esters are converted to polyol polyesters by base-catalyzed transesterification. In addition, atmospheric oxidation at nonconjugated double bonds substantially increases their susceptibility to conjugation. Pretreatment of lower alkyl fatty esters in accordance with the present invention results in the formation of these color bodies (and/or their precursors) and their separation from the lower alkyl fatty esters prior to reaction of the lower alkyl fatty esters with polyols to form polyol polyesters. Thus, when the polyol polyester preparation is carried out using lower alkyl fatty esters which have been previously treated by the process herein, color formation in the polyol polyester reaction product is substantially reduced or eliminated.

Since very small quantities of color bodies can result in undesirable color in the finished polyol polyesters, the present invention is applicable to treatment of lower alkyl fatty esters wherein as low as about 0.1 weight percent of the fatty acid moieties in said esters contain conjugated or conjugatable sites of unsaturation. Typically, the lower alkyl fatty esters which are treated in accordance with this invention will contain 0.5 weight percent or more of fatty acid moieties which have conjugated or conjugatable sites of unsaturation. More typically, the percentage of such fatty acid moieties in the lower alkyl fatty esters will be from about 5 to about 45 weight percent.

All percentages and ratios herein are "by weight" unless specified otherwise.

In the pretreatment process herein, the lower alkyl fatty esters are subjected to a three step process.

In Step (A) the lower alkyl fatty esters, in a liquid state, are contacted with an alkoxide base. The alkoxide base may be used in the form of a dry powder or an alcoholic solution containing from about 5% to about 30% alkoxide base. The amount of alkoxide base used in contacting the lower alkyl fatty esters should be sufficient to provide a weight ratio of alkoxide base to ester of at least about 0.005:1, preferably from about 0.01 to about 0.05:1, and most preferably from about 0.01:1 to about 0.02:1. The contact should be at time of for about 10 to about 120 (preferably from about 30 to about 60) minutes, at a temperature of from about 60° C. to about 140° C., preferably from about 60° C. to about 120° C., and most preferably from about 80° C. to about 100° C. Dark color bodies will form in this step.

In Step (B) the esters are separated from the alkoxide and any undissolved color bodies. This is accomplished, e.g., by centrifugation or filtration. After separation from the alkoxide and any undissolved color bodies the esters are clear, but have a brownish yellow color due to the presence of dissolved color bodies.

In Step (C) the separated esters from Step (B) are distilled. The conditions of distillation are within the range of from about 145° C. to about 250° C. at from about 1 mm to about 50 mm Hg. The specific distillation conditions chosen for a particular lower alkyl fatty ester product will depend upon the boiling characteristics of that ester product. The distilled esters are clear and water white.

The alkoxide bases used in the pretreatment of the lower alkyl fatty esters in Step (A) of the present invention have the formula $(RO)_nM$, wherein R is an alkyl radical of from 1 to about 5 carbon atoms, M is an alkali metal (i.e., a metal from Group IA of the Periodic Table of Elements), an alkaline earth metal (i.e., a metal from Group IIA of the Periodic Table of Elements) or aluminum, and n is 1 when M is alkali metal, 2 when M is alkaline earth metal, and 3 when M is aluminum. The term "alkyl" in describing the alkoxide bases includes unsubstituted alkyl and substituted alkyl radicals such as, for example, benzyl, haloalkyl, nitroalkyl, and the like. Preferred bases are those wherein R contains from 1 to 4 carbon atoms. Examples of bases for use in the present invention are: sodium methoxide, potassium methoxide, sodium ethoxide, sodium 2-chloroethoxide, lithium ethoxide, sodium propoxide, potassium propoxide, sodium isopropoxide, sodium butoxide, calcium diethoxide, magnesium diisopropoxide, barium dibutoxide, aluminum triisopropoxide and aluminum tritertiarybutoxide. As is known in the art, these bases in which M is an alkali metal are made by reacting the corresponding alcohol (e.g., ethanol to make the ethoxide) with the alkali metal or its hydride. Bases in which M is aluminum are made by reacting aluminum chloride with the alkali metal alkoxide of the corresponding alcohol (e.g., reacting one mole of aluminum chloride with three moles of sodium isopropoxide to make one mole of aluminum triisopropoxide).

The preferred alkoxide bases for pretreatment of the lower alkyl fatty esters are the alkali metal alkoxides, e.g., sodium and potassium alkoxides, especially the sodium and potassium methoxides and ethoxides.

In the preparation of polyol polyesters of improved color (i.e., having reduced color content) the lower alkyl fatty esters which have been pretreated as described above are reacted in the presence of a basic catalyst in accordance with known procedures. See for example U.S. Pat. No. 2,893,990, Hass et al., issued July 7, 1959. A preferred procedure is that described in U.S. Pat. No. 4,517,360, Volpenhein, issued May 14, 1985, and incorporated by reference herein. According to this process, a molten mixture is formed containing the lower alkyl fatty ester, the polyol, an alkali metal fatty acid soap, and the basic catalyst which is selected from sodium carbonate, potassium carbonate, barium carbonate, or mixtures thereof. The mixture contains from 10% to 50% polyol, from 40% to 80% lower alkyl fatty ester, from 1% to 30% of the soap, and from 0.05% to 5% of the basic catalyst. Preferably the molar ratio of soap:polyol is from about 0.75:1 to about 1:1. Excess lower alkyl fatty ester is then added to this melt, the amount being sufficient to raise the overall ester:polyol mole ratio above 8:1, and the mixture is reacted at a temperature of from about 120° C. to 160° C. and pressure of from about 0.1 to 10 mm Hg for about 2 to 8 hours. The fatty polyol polyesters can then be separated from the reaction mix by conventional means such as solvent extraction, water washing, etc.

The present invention will be illustrated by the following example.

EXAMPLE I

The oil (triglyceride) derived by the partial hydrogenation of refined soybean oil is converted to the methyl ester by methanolysis in the presence of potassium carbonate, and distilled. The Iodine Value of the starting oil is approximately 80. The distilled crude methyl ester is clear and nearly water white. Based on the Iodine Value of partially hydrogenated soybean oil, it is estimated that the percentage of the fatty acid moieties in the methy ester which contains conjugated or conjugatable sites of unsaturation is about 20%. The batch of distilled ester is split in half and one portion is treated with potassium methoxide. Powdered potassium methoxide (1% by weight of the methyl ester) is added to the stirring methyl ester and the mixture is heated to 90° C. for 1 hour. A highly colored solid precipitates, and is subsequently separated from the ester by centrifugation. The centrifuged methyl ester, which is clear but highly colored, is then distilled at 180° C. and 1 mm Hg, yielding a near water white methyl ester.

The second portion of the distilled crude methyl ester is redistilled without having been heated with methoxide. This redistilled ester is also clear and essentially water white.

A sample from the portion of methyl ester treated with potassium methoxide in accordance with the present invention and a sample from the portion which was not treated with potassium methoxide are both converted to sucrose polyester according to the procedure of U.S. Pat. No. 4,517,360.

6.3 gm of potassium hydroxide (85% KOH) is dissolved in 25 gm methanol, and allowed to stir on a magnetic stirrer.

254 gm of methyl ester is added to a three-neck flask fitted with a mechanical agitator, thermometer, reflux condenser, and heating mantle. Slow agitation is started and the methanolic potassium hydroxide solution is added to the stirring methyl esters. The mixture is heated under a nitrogen blanket to reflux and held there for 20 minutes.

The reflux condenser is then converted to allow distillation of methanol that will occur in the next step.

51 gm of sucrose and 2.1 gm of potassium carbonate are added to the stirring mixture. Heating is continued allowing the slow distillation of methanol from the mixture. When the methanol is removed the temperature is allowed to rise to 100° C.

Full vacuum is slowly applied (1–5 mm Hg) and the temperature is raised to 135° C. Temperature is held at 135° C. for 1.5 hours until the sucrose is partially esterified and drawn into solution.

Pressure is brought to atmospheric with nitrogen and an additional 309 gm of methyl ester is added to the mixture.

Full vacuum (1–5 mm Hg) is applied slowly, and the reaction is continued at full vacuum and about 135° C. for four hours.

The reaction is then cooled to below 100° C. and 25 ml of distilled water is added to hydrate the potassium soap formed in the mixture. The soap sludge is then removed by centrifugation.

The oil produced in the reaction is then washed three times with water at approximately 60° C. and the washed oil then dried on a Rotovap ®.

The oil is bleached at approximately 60° C. with 17 gm of bleaching earth and is then filtered.

Excess methyl ester is removed by thin film evaporation at high vacuum, and the product deodorized by steam distillation.

The resulting sucrose polyester (SPE) oil produced from the portion of methyl esters which was not treated with potassium methoxide is darker in color than the oil produced from the treated esters, which is essentially water white in appearance. The oils are evaluated for color as 10% solutions in hexane on a UV/Visible spectrometer and the absorbance values at 440 and 520 nm are reported in Table 1. These values are consistent with the visible appearance of the oils, i.e., more color in the oil prepared with the untreated methyl esters.

TABLE 1

| | Finished SPE Oil* Visible | |
|---|---|---|
| Ester Treatment | Absorbance 440 | (nm) 520 |
| KOCH$_3$ | 0.038 | 0.029 |
| None | 0.062 | 0.045 |

*10% solution in heptane

What is claimed is:

1. A process for treatment of $C_1$–$C_3$ alkyl esters of $C_6$–$C_{22}$ fatty acids wherein at least 0.1% by weight of the fatty acid moieties contain conjugated or conjugatable sites of unsaturation, said process comprising the steps of:

(A) contacting said $C_1$–$C_3$ alkyl esters of fatty acids in a liquid state with an alkoxide base at a temperature of from about 60° C. to about 140° C. for from about 10 minutes to about 120 minutes, the said alkoxide base having the formula $(RO)_nM$, wherein R is an alkyl radical of from 1 to about 5 carbon atoms, M is an alkali metal, an alkaline earth metal or aluminum, and n is 1 when M is alkali metal, 2 when M is alkaline earth metal, and 3 when M is aluminum, and wherein the weight ratio of alkoxide base to ester is at least 0.005:1;

(B) separating undissolved solids from the liquid esters of Step A; and (C) distilling the liquid esters from Step B and collecting the distilled esters.

2. The process of claim 1 wherein at least 0.5% by weight of the fatty acid moieties of the esters contain conjugated or conjugatable sites of unsaturation.

3. The process of claim 2 wherein M in the alkoxide is an alkali metal.

4. The process of claim 3 wherein in Step (B), the separation is done by centrifugation.

5. The process of claims 1, 2, 3 or 4 wherein the esters are methyl esters.

6. A process for preparing polyol polyesters of improved color from polyols and $C_1$–$C_3$ alkyl esters of $C_6$–$C_{22}$ fatty acids in which at least 0.1% by weight of the fatty acid moieties in said $C_1$–$C_3$ alkyl fatty esters contain conjugated or conjugatable sites of unsaturation, the said process comprising:

I. Pretreating said $C_1$–$C_3$ alkyl fatty esters by a process comprising the steps of:

(A) contacting said $C_1$–$C_3$ alkyl fatty esters in a liquid state with an alkoxide base at a temperature of from about 60° C. to about 140° C. for from about 10 minutes to about 120 minutes, the said alkoxide base having the formula $(RO)_nM$, wherein R is an alkyl radical of from 1 to about 5 carbon atoms, M is an alkali metal, an alkaline earth metal or aluminum, and n is 1 when M is alkali metal, 2 when M is alkaline earth metal, and 3 when M is aluminum, and wherein the weight ratio of alkoxide base to ester is at least 0.005:1;

(B) separating undissolved solids from the liquid $C_1$–$C_3$ alkyl fatty esters of Step A;

(C) distilling the liquid $C_1$–$C_3$ alkyl fatty esters from Step B and collecting the distilled esters; and II. Reacting the distilled $C_1$–$C_3$ alkyl fatty esters from I(C) with a polyol in the presence of a basic catalyst and concurrently removing from the reaction mix the $C_1$–$C_3$ alcohol formed during the reaction.

7. The process of claim 6 wherein at least 0.5% by weight of the fatty acid moieties of the $C_1$–$C_3$ alkyl fatty esters contain conjugated or conjugatable sites of unsaturation.

8. The process of claim 7 wherein the alkyl fatty esters are methyl esters.

9. The process of claim 8 wherein the M in the alkoxide base is an alkali metal.

10. The process of claims 7, 8 or 9 wherein in Step II the polyol is selected from the group consisting of monosaccharides, disaccharides and sugar alcohols.

11. The process of claim 10 wherein Step II is carried out by a process comprising the steps of:

i. forming a molten mixture of the $C_1$–$C_3$ alkyl fatty ester, an alkali metal fatty acid soap and a basic catalyst selected from sodium carbonate, potassium carbonate, barium carbonate, and mixtures thereof, said molten mixture containing from about 10% to about 50% polyol, from about 40% to about 80% $C_1$–$C_3$ alkyl fatty ester, from about 1% to about 30% of the soap and from about 0.05% to about 5% of the basic catalyst;

ii. adding excess $C_1$–$C_3$ alkyl fatty ester to the melt of (i), the amount of $C_1$–$C_3$ alkyl fatty ester being sufficient to raise the overall ester:polyol mole ratio above about 8:1;

iii. reacting the mixture from (ii) at about 120° C. to about 160° C. and a pressure of 0.1 to about 10 mm Hg for from about 2 to about 8 hours; and iv. separating the polyol polyester from the reaction mix.

* * * * *